(12) United States Patent
Xu et al.

(10) Patent No.: US 8,999,706 B2
(45) Date of Patent: Apr. 7, 2015

(54) METHODS FOR PREPARATION OF HUMAN HAIR-FOLLICLE DERIVED MULTIPOTENT ADULT STEM CELLS

(75) Inventors: Xiaowei Xu, Monmouth Junction, NJ (US); Hong Yu, Philadelphia, PA (US); Douglas Dong Fang, San Diego, CA (US); Meenhard Herlyn, Wynnewood, PA (US)

(73) Assignees: The Trustees of the University of Pennsylvania, Philadelphia, PA (US); The Wistar Institute of Anatomy and Biology, Philadelphia, PA (US)

( * ) Notice: Subject to any disclaimer, the term of this patent is extended or adjusted under 35 U.S.C. 154(b) by 1204 days.

(21) Appl. No.: 11/911,400

(22) PCT Filed: Apr. 12, 2006

(86) PCT No.: PCT/US2006/013636
§ 371 (c)(1),
(2), (4) Date: Jun. 18, 2008

(87) PCT Pub. No.: WO2006/110806
PCT Pub. Date: Oct. 19, 2006

(65) Prior Publication Data
US 2009/0130065 A1     May 21, 2009

Related U.S. Application Data

(60) Provisional application No. 60/671,025, filed on Apr. 12, 2005, provisional application No. 60/687,804, filed on Jun. 6, 2005.

(51) Int. Cl.
*C12N 5/00*     (2006.01)
*C12N 15/00*    (2006.01)
(Continued)

(52) U.S. Cl.
CPC ............ *C12N 5/0607* (2013.01); *C12N 5/0628* (2013.01); *C12N 2500/44* (2013.01); *C12N 2501/11* (2013.01); *C12N 2501/115* (2013.01)

(58) Field of Classification Search
USPC .................................................. 435/325, 455
See application file for complete search history.

(56) References Cited

U.S. PATENT DOCUMENTS 5,130,142 A * 7/1992 Wong et al. ................... 424/574
5,556,783 A   9/1996 Lavker
(Continued)

OTHER PUBLICATIONS

Shi et al. "Identification of hematopoietic cell populations from the dermal papillae of human hair follicles", Transplantation Proceeding, 2004, 36:3208-3211.*

(Continued)

*Primary Examiner* — Michael C. Wilson
(74) *Attorney, Agent, or Firm* — Patrick J. Hagan; Dann, Dorfman, Herrell and Skillman, P.C.; Kathleen D. Rigaut (57) ABSTRACT

Isolated human multipotent adult stem cell and isolated populations of cells that include human multipotent adult stem cells are disclosed. Human hair-follicle derived multipotent adult stem cells and methods of preparing isolated populations of cells that include human multipotent adult stem cells are disclosed. Isolated human hair-follicle derived multipotent adult stem cell that can differentiate in culture into a neuronal cell, a glial cell, a melanocyte cell, a muscle cell, an osteocyte, a chondrocyte, and a lymphocyte. Isolated human hair-follicle derived multipotent adult stem cell that can grow in cell culture in spheres are disclosed. Human pancreas derived multipotent adult stem cells, human liver derived multipotent adult stem cells, human kidney derived multipotent adult stem cells, human heart derived multipotent adult stem cells, human neural derived multipotent adult stem cells and methods of preparing isolated populations of cells that include such human multipotent adult stem cells are disclosed. Method of treating an individual who has diabetes, cardiac muscle damage, muscle damage and disease, neurodegenerative disease or nerve damage or injury, bone loss, damage and/or disease, cartilage loss, damage and/or disease, hair loss and immune disorders, are disclosed.

2 Claims, 6 Drawing Sheets

(51) Int. Cl.
*C12N 5/074* (2010.01)
*C12N 5/071* (2010.01)

(56) References Cited

U.S. PATENT DOCUMENTS

| | | | |
|---|---|---|---|
| 6,015,671 A | 1/2000 | Field | |
| 6,599,912 B1 * | 7/2003 | Au et al. | 514/283 |
| 6,866,843 B2 | 3/2005 | Habener | |
| 7,011,828 B2 | 3/2006 | Reubinoff | |
| 7,115,415 B2 * | 10/2006 | Goddard et al. | 435/325 |
| 7,919,319 B2 * | 4/2011 | Jervis et al. | 435/395 |
| 8,153,428 B2 * | 4/2012 | Carpenter et al. | 435/377 |
| 2002/0068045 A1 | 6/2002 | Reubinoff | |
| 2002/0160509 A1 | 10/2002 | Reubinoff | |
| 2002/0164308 A1 | 11/2002 | Reubinoff | |
| 2003/0077823 A1 * | 4/2003 | Li et al. | 435/366 |
| 2003/0198614 A1 * | 10/2003 | Takahashi et al. | 424/70.1 |
| 2005/0037492 A1 * | 2/2005 | Xu et al. | 435/366 |
| 2005/0054098 A1 * | 3/2005 | Mistry et al. | 435/372 |

OTHER PUBLICATIONS

Shi (Transplantation Proceedings, Dec. 2004, vol. 36, p. 3208-3211).*
Lako (J. Cell Sci., Oc. 15, 2002, No. 15, p. 3967-3974).*
Ma (Ann Acad Med Singapore, 2004, vol. 33, p. 783-788).*
Terskikh (Rossiiskaia Akademiia Nauk, Nov.-Dec. 2001, vol. 6, p. 738-744).*
Yu (J. Investigative Dermatology, 2010, vol. 130, p. 1227-1236).*
Amoh (J. Dermatological Sci., 2010, vol. 60, p. 131-137).*
Cavaleri et al., "Nanog: A New Recruit to the Embryonic Stem Cell Orchestra" Cell (2003) 113:551-552.
Clark et al., "Human STELLAR, NANOG, and GDF3 Genes Are Expressed in Pluripotent Cells and Map to Chromosome 12p13, a Hotspot for Teratocarcinoma" Stem Cells (2004)22:169-179.
Clark et al., "Spontaneous differentiation of germ cells from human embryonic stem cells in vitro", Human Mol. Genet., (2004) 13:727-739.
Deutsch, et al., "A bipotential precursor population for pancreas and liver within the embryonic endoderm", Development (2001) 128:871-881.
Fischback et al., "Stem cells: science, policy, and ethics.", J. of Clin. Invest., (2004) 114:1364-1370.
Gronthos, et al., "Surface protein characterization of human adipose tissue-derived stromal cells.", J. Cell. Physiol. (2001) 189:54-63.
Hansis et al., "Oct-4 expression in inner cell mass and trophectoderm of human blastocysts.", Mol. Hum. Reprod. (2000) 6:999-1004.
Jaruzelska et al., "Conservation of a Pumilio-Nanos complex from *Drosophila* germ plasm to human germ cells.", Dev. Genes Evol. (2003) 213:120-126.
Jiang, et al., "Pluripotency of mesenchymal stem cells derived from adult marrow", Nature (2002) 418:41-9.
Lemoli et al., "Stem cell plasticity: time for a reappraisal?", Haematologica (2005) 90: 360-81.
Lee et al., "Human Mesenchymal Stem Cells Maintain Transgene Expression during Expansion and Differentiation", Molecular Therapy, 2001, 3(6): 857-866.
McKay, "Stem cells in the central nervous system.", Science (1997) 276:66-71.
Moore et al., "Human Pumilio-2 is expressed in embryonic stem cells and germ cells and interacts with DAZ (Deleted in AZoospermia) and DAZ-like proteins.", Proc. Natl. Acad. Sci. USA (2003) 100:538-543.
Niwa et al., "Quantitative expression of Oct-3/4 defines differentiation, dedifferentiation or self-renewal of ES cells.", Nat. Genet. (2000) 24:372-376.
Pittenger, et al., "Multilineage potential of adult human mesenchymal stem cells.", Science (1999) 284:143-147.
Yoon, et al., "Clonally expanded novel multipotent stem cells from human bone marrow regenerate myocardium after myocardial infarction", J. Clin. Invest., (2005) 115: 326-338.
Shihabuddin, et al., "The search for neural progenitor cells: prospects for the therapy of neurodegenerative disease", Mol. Med. Today (1999) 5:474-480.
Toma, et al., "Isolation of multipotent adult stem cells from the dermis of mammalian skin", Nature Cell Biol. (2001) 3:778-784.

* cited by examiner

MITF

Control | Differentiated

METHODS FOR PREPARATION OF HUMAN HAIR-FOLLICLE DERIVED MULTIPOTENT ADULT STEM CELLS

CROSS-REFERENCE TO RELATED APPLICATIONS

This application is the U.S. National Stage filing of International Application Serial No. PCT/US2006/013636 filed Apr. 12, 2006, which claims priority to U.S. Provisional Patent Application No. 60/671,025, filed Apr. 12, 2005, and 60/687,804, filed Jun. 6, 2005, each of which is incorporated herein by reference in its entirety.

This application claims priority to U.S. Provisional Application No. 60/671,025 filed Apr. 12, 2005 and U.S. Provisional Application No. 60/687,804 filed Jun. 6, 2006, the disclosures of which are each incorporated herein by reference.

FIELD OF THE INVENTION

The present invention relates to isolated human multipotent adult stem cells, isolated populations of cells comprising such cells, and methods of making and using the same.

BACKGROUND OF THE INVENTION

A stem cell (SC) is characterized by two properties: 1) the unique capacity for self-renewal (a stem cell is able to divide into identical progeny cells indefinitely, perhaps throughout the entire life of the organism), and 2) in response to a signal such as a growth factor, to give rise to a cell containing an altered pattern of gene expression and a more restricted developmental potential than its parent. Eventually, a SC becomes known as a "progenitor" or "precursor" cell, committed to producing one or a few terminally differentiated cells such as neurons or muscle cells (Fischback, et al., 2004, J. of Clin. Invest., 114:1364-1370). Thus, in contrast to the large majority of cells in the body committed to a specific function, SCs are uncommitted and remain so until they receive a signal to generate specialized cells.

A totipotent cell is a stem cell not committed to a specific lineage, which is capable of giving rise to all types of differentiated cells and tissues, including extraembryonic tissues. The only type of totipotent stem cell is the fertilized egg. Soon after fertilization, in the earliest stages of embryogenesis, a zygote is formed by the fusion of the egg and sperm, and the zygote and its progeny divide several times to form a ball of 32 to 128 cells called a "morula.". Each cell of the morula is totipotent in that each one can give rise to all cell types in the embryo plus all of the extraembryonic tissues necessary for implantation in the uterine wall. As cells of the morula continue to proliferate, the morula enlarges to form a hollow sphere called a blastocyst. Next, but still prior to implantation, a few cells delaminate from the surface layer of the blastocyst to form an inner cell mass (ICM) within the cavity. Blastocysts created in vitro also contain an ICM, and it is possible to isolate cells from the ICM of human blastocysts and grow them in tissue culture. Cells isolated from the ICM are pluripotent, as they can become any of the hundreds of cell types in the adult body, but they are not totipotent because they cannot contribute to extraembryonic membranes or the formation of the placenta (Fischback, et al., 2004, J. of Clin. Invest., 114:1364-1370). Thus, a single pluripotent SC has the ability to give rise to cells originating from all three germ layers: mesoderm, endoderm, and ectoderm. The only known sources of human pluripotent SCs are those isolated and cultured from the inner cell mass of the blastocyst, known as embryonic stem cells (ESCs), and those isolated from the primordial germ cells of the gonadal ridge of 5- to 10-week fetuses or embryonic germ cells (EGCs) (Lemoli, et al., 2005, Haematologica, 90:360-81).

In undifferentiated human ESCs, several marker genes have been shown to be expressed and may play a role in pluripotent capacity. These include, but are not limited to, the POU-domain transcription factor OCT4 (Hansis, et al., 2000, Mol. Hum. Reprod., 6: 999-1004; Niwa, et al., 2000, Nat. Genet., 24, 372-376); Growth and Differentiation Factor 3 (GDF3), Nanog, stella-related (STELLAR) gene (Clark, et al., 2004, Stem Cells, 22: 169-179); Pumilio-2 (PUM2) (Moore, et al., 2003, Proc. Natl. Acad. Sci. USA, 100: 538-543) and Nanos 1 (Jaruzelska, et al., 2003, Dev. Genes Evol., 213: 120-126; Clark, et al., 2004, Human Mol. Genet., 13: 727-739; Cavaleri, et al., 2003, Cell, 113: 551-557).

SCs have also been identified in nonembryonic tissues. Adult SCs are undifferentiated cells present in various differentiated mature tissues. Like ESCs, adult SCs are undifferentiated, but are considered to be multipotent, having the potential to give rise to a more limited number of cell types. Adult SCs are capable of differentiation into the cell types from the tissue that the adult stem cell originated. Furthermore, in the past decade, adult SCs have been found in tissues that were not previously believed to harbor them, such as the central nervous system. Adult SCs have been derived from the nervous system (McKay, 1997, Science 276:66-71; Shihabuddin, et al., 1999, Mol. Med. Today 5:474-480), bone marrow (Pittenger, et al., 1999, Science 284:143-147; Pittenger, et al., 2001, in: Mesenchymal stem cells of human adult bone marrow. Marshak, D. R., Gardner, D. K., and Gottlieb, D. eds., Cold Spring Harbor, N.Y.: Cold Spring Harbor Laboratory Press, 349-374); adipose tissue (Gronthos, et al., 2001, J. Cell. Physiol. 189:54-63), dermis (Toma, et al., 2001, Nature Cell Biol. 3:778-784) and pancreas and liver (Deutsch, et al., 2001, Development 128:871-881) and other organs (Lemoli, et al., 2005, Haematologica, 90:360-81).

Notably, SC derived from adult tissues such as the bone marrow (BM), the skeletal musculature, or the central nervous system (CNS) have been recently reported to have a more plasticity in differentiation potential than was originally believed to be possible for adult SCs. In the last few years, a number of different groups have claimed that adult mammalian SCs may be capable of differentiating across tissue lineage boundaries and that this capacity to transdifferentiate into mature cells of different origin may represent a novel therapeutic strategy for tissue regeneration. (Lemoli, et al., 2005, Haematologica, 90:360-81). For example, a subset of adult mesenchymal stem cells (MSCs) derived from bone marrow have been reported to be pluripotent (Jiang, et al., 2002, Nature, 418:41-9). Additionally, a subpopulation of stem cells within adult human BM were reported to self-renew without loss of multipotency for more than 140 population doublings and exhibit the capacity for differentiation into cells of all 3 germ layers. These multipotent stem cells from human BM were reported to regenerate myocardium after myocardial infarction (Yoon, et al., 2005, J. Clin. Invest., 115: 326-338).

Adult stem cells are the focus of intensive research aimed at developing transplantation strategies to promote recovery in the diseased or injured tissues. Adult stem cells are maintained in the niche microenvironment. Transdifferentiation of an adult SC into a non-canonical progeny, e.g., muscle or liver from BM SC, has been a rare phenomenon, usually associated with severe damage in the target tissue, and often with a specific selective pressure for the trans-differentiated progeny. Furthermore, some of the reports were not confirmed in subsequent investigations; for instance, the muscle-derived SC reported to give rise to hematopoietic SC upon transplantation were subsequently shown to be hematopoietic in origin. In other cases, cell fusion rather than transdifferentiation was demonstrated to be the main mechanism of the observed plasticity of adult SC. Nevertheless, the hope of finding pluripotency in adult SCs has an obvious relevance for regenerative medicine. The possibility of using SC from easily accessible sources to repair or regenerate tissues severely damaged by diseases such as muscular dystrophy, diabetes mellitus, Alzheimer's, or hepatitis, or by vascular conditions, autoimmune disorders, congenital and/or degenerative disorders, disease or trauma, such as infarcted myocardium, cirrhotic liver, connective tissue damaged by rheumatic disease, would have a dramatic therapeutic impact on otherwise untreatable conditions (Lemoli, et al., 2005, Haematologica, 90:360-81) as well as on basic research, drug discovery, treatment and prevention of disease.

Hair follicles have a well defined epithelial stem cell niche: the bulge, which is a well-demarcated structure within the lower permanent portion of hair follicles. Bulge epithelial stem cells have limited differential potential and have been shown to give rise to only squamous and sebaceous cells. Hair color is determined by melanocytes in the hair bulb at the base of hair follicles. While melanocyte precursor cells were postulated in the bulge area as shown in melanocyte-targeted (Dct)-lacZ transgenic mice, these cells have not be isolated and it is unknown whether they are present in human hair follicles.

Thus, there remains a great need for methods of isolating new sources of pluripotent SCs, especially those bearing the genetic hallmarks of early embryonic SCs.

SUMMARY OF THE INVENTION

The present invention relates to isolated human hair-follicle derived multipotent adult stem cells that expresses one or more of: nanog, Oct4 and Nestin.

The present invention relates to isolated human hair-follicle derived multipotent adult stem cells that can differentiate in culture into one or more of the following: neuronal cells, glial cells, melanocytic cells, muscle cells, adipocytes, osteocytes, chondrocytes, islet cells, and lymphocytes.

The present invention relates to isolated human hair-follicle derived multipotent adult stem cells that grows in cell culture in spheres.

The present invention relates to isolated human multipotent adult stem cells selected from the group consisting of: an isolated human multipotent adult stem cell that expresses nanog and; an isolated human multipotent adult stem cell that expresses Oct4, is free of stage specific embryonic antigen-3 and stage specific embryonic antigen-4; and an isolated human multipotent adult stem cell that expresses nanog and Oct4 and is free of stage specific embryonic antigen-3 and stage specific embryonic antigen-4.

The present invention relates to isolated populations of human multipotent adult stem cells selected from the group consisting of:
human multipotent adult stem cells that express nanog and are free of stage specific embryonic antigen-3 and stage specific embryonic antigen-4;
human multipotent adult stem cells that express Oct4 and are free of stage specific embryonic antigen-3 and stage specific embryonic antigen-4;
human multipotent adult stem cells that express Nestin and are free of stage specific embryonic antigen-3 and stage specific embryonic antigen-4;
human multipotent adult stem cells that express nanog and Oct4 and are free of stage specific embryonic antigen-3 and stage specific embryonic antigen-4; and
combinations thereof.

The present invention relates to isolated populations of human hair-follicle derived multipotent adult stem cells selected from the group consisting of:
human hair-follicle derived multipotent adult stem cells that express nanog;
human hair follicle-derived multipotent adult stem cells that express Oct4;
human hair follicle-derived multipotent adult stem cells that express Nestin;
human hair-follicle derived multipotent adult stem cells that express nanog and Oct4; and
combinations thereof.

The present invention relates to isolated populations of human hair-follicle derived multipotent adult stem cells that can differentiate in culture into one or more of the following: neuronal cells, glial cells, melanocytic cells, muscle cells, adipocytes, osteocytes, chondrocytes, islet cells, lymphocytes.

The present invention relates to isolated populations of human hair-follicle derived multipotent adult stem cell that grows in cell culture in spheres.

The present invention relates to methods of preparing an isolated population of human hair-follicle derived multipotent adult stem cells. The methods comprising the steps of forming a single cell suspension of cells disassociated from follicular epithelium of a hair shaft and culturing such cells in conditions suitable for culturing and maintaining human embryonic stem cells wherein spheres form that comprise human hair-follicle derived multipotent adult stem cells or in conditions comprising a serum free minimal medium supplemented with human basic fibroblast growth factor and human epidermal growth factor.

The present invention relates to methods of preparing an isolated populations of human hair-follicle derived multipotent adult stem cells comprising a human hair follicle in conditions suitable for culturing and maintaining human embryonic stem cells wherein spheres form that comprise human hair-follicle derived multipotent adult stem cells or in conditions comprising a serum free minimal medium supplemented with human basic fibroblast growth factor and human epidermal growth factor, wherein said hair follicle is cultured under such conditions for a time sufficient for cells to grow on said hair follicle, and isolating from said cells a population of human hair-follicle derived multipotent adult stem cells.

The present invention relates to methods of treating an individual who has diabetes.

The present invention relates to methods of treating an individual who has cardiac muscle damage.

The present invention relates to methods of treating an individual who has muscle damage or disease.

The present invention relates to methods of treating an individual who has a neurodegenerative disease.

The present invention relates to methods of treating an individual who has nerve damage or injury.

The present invention relates to methods of treating an individual who has hair loss.

The present invention relates to methods of treating an individual who has bone loss, damage and/or disease.

The present invention relates to methods of treating an individual who has cartilage loss, damage and/or disease.

The present invention relates to methods of treating an individual comprising the steps of: preparing an isolated population of human multipotent adult stem cells by forming a single cell suspension of cells disassociated from sample that comprises cells from an individual, and culturing such cells in conditions suitable for culturing and maintaining human embryonic stem cells or in conditions comprising a serum free minimal medium supplemented with human basic fibroblast growth factor and human epidermal growth factor; wherein multipotent adult stem cells are identified and isolated from said culture; and administering to said individual isolated cells.

The present invention relates to methods of preparing an isolated population of human multipotent adult stem cells. The methods comprise the steps of: a) forming a single cell suspension of cells disassociated from sample that comprises cells from an individual, and) culturing such cells in conditions suitable for culturing and maintaining human embryonic stem cells or in conditions comprising a serum free minimal medium supplemented with human basic fibroblast growth factor and human epidermal growth factor; wherein multipotent adult stem cells are identified and isolated from said culture.

The present invention relates to methods of treating an individual comprising administering to said individual isolated cells prepared by methods that comprise the steps of: a) forming a single cell suspension of cells disassociated from sample that comprises cells from an individual, and) culturing such cells in conditions suitable for culturing and maintaining human embryonic stem cells or in conditions comprising a serum free minimal medium supplemented with human basic fibroblast growth factor and human epidermal growth factor; wherein multipotent adult stem cells are identified and isolated from said culture.

BRIEF DESCRIPTION OF THE FIGURES

Panel A. Telogen hair before typsin treatment
Panel B. Anagen hair before trypsin treatment
Panel C. Single cells from hair follicles attached after trypsin treatment
Panel D. Single cells from hair follicles attached after trypsin treatment
Panel E. A small aggregate forms after 3-7 days of incubation in hESC medium
Panel F. A small aggregate forms after 3-7 days of incubation in hESC medium
Panel G. A small hair sphere forms after 3 weeks of incubation in hESC medium
Panel H. A well formed hair sphere forms after 6 weeks of incubation in hESC medium
Panel I. In limiting dilution assay, a hair sphere derived single cell attached
Panel J. In limiting dilution assay, two cells attached after 24 hours incubation in the hESC medium
Panel K. A small aggregate forms after 1 week incubation
Panel L. A well formed hair sphere formed 8 weeks after initial attachment in limiting dilution assay

Panel A. Confocal image of nestin stains cytoplasm of a hair sphere derived small round cells.
Panel B. Confocal image of DAPI stains nucleus
Panel C. Merged image of nestin and DAPI stains
Panel D. Confocal image of nestin stains cytoplasm of a hair sphere derived spindled cells.
Panel E. Confocal image of DAPI stains nucleus
Panel F. Merged image of nestin and DAPI stains
Panel G. Confocal image of Oct4 stain shows characteristic puntated nuclear staining pattern of a small round cell.
Panel H. Confocal image of DAPI stains nucleus
Panel I. Merged image of Oct4 and DAPI stains
Panel J. Confocal image of Oct4 (low power) shows characteristic puntated nuclear staining pattern in a small cluster of cells of variable size.
Panel K. Confocal image of DAPI stains nucleus
Panel L. Merged image of nestin and DAPI stains
Panel M. Confocal image of Nanog stains nuclei of a small cluster of hair sphere derived small round cells.
Panel N. Confocal image of DAPI stains nucleus
Panel O. Merged image of nestin and DAPI stains

Panel A. Mitf and Tryp1 gene expression before and after culture in melanocytic differentiation medium
Panel B. After melanocytic differentiation, the cells have long processes.
Panel C. Fontana Mason stain shows melanin pigment in differentiated cells
Panel D. Confocal image of Mitf stains nuclei of differentiated cells
Panel E. Confocal image of DAPI stains nuclei
Panel F. Merged image of Mitf and DAPI stains
Panel G. Tyrosinase staining of skin reconstruct with undifferentiated cells
Panel H. Tyrosinase staining of skin reconstruct with melanocytic differentiated cells shows tyrosinase positive cells present at the dermal epidermal junction.
Panel I. Fontana Mason staining of skin reconstruct with undifferentiated cells
Panel J. Fontana Mason staining of skin reconstruct with melanocytic differentiated cells shows melanin pigment positive cells present at the dermal epidermal junction.

Panel A. MAP2 and β3 tubulin, calponin and desmin gene expression after culture in neuron and smooth muscle differentiation medium
Panel B. Confocal image of MAP2 stains dendritic process of neuron differentiated cells
Panel C. Confocal image of DAPI stains nuclei
Panel D. Merged image of MAP2 and DAPI stains
Panel E. Confocal image of Neurofilament stains cytoplasm of neuron differentiated cells
Panel F. Confocal image of DAPI stains nuclei
Panel G. Merged image of Mitf and DAPI stains
Panel H. Confocal image of chromogranin stains cytoplasm of neuron differentiated cells
Panel I. Confocal image of DAPI stains nuclei
Panel J. Merged image of Mitf and DAPI stains
Panel K. Confocal image of smooth muscle actin stains cytoplasm of smooth muscle differentiated cells Panel L. Confocal image of DAPI stains nuclei
Panel M. Merged image of Mitf and DAPI stains
FIG. 4 shows that Stem cells are located in the bulge area of hair follicles. Individual hair follicles were cultured in the hESC cells for 6 days before staining.
Panel A. Oct4 staining of outer root sheet
Panel B. Direct view image of outer root sheath
Panel C. Merged image of Oct4 staining with direct view image
Panel D. Oct4 staining of telogen bulge
Panel E. Direct view image of telogen bulge
Panel F. Merged image of Oct4 staining with direct view image
Panel G. Nestin staining of outer root sheet
Panel H. Direct view image of outer root sheath
Panel I. Merged image of Nestin staining with direct view image
Panel J. Nestin staining of telogen bulge
Panel K. Direct view image of telogen bulge
Panel L. Merged image of Nestin staining with direct view image
Panel M. Confocal image of Oct4 stain of outer root sheath
Panel N. DAPI stain of nuclei
Panel O. Merged image of Oct 4 and DAPI stains
Panel P. Confocal image of Oct4 stain of telogen bulge
Panel Q. DAPI stain of nuclei
Panel R. Merged image of Oct 4 and DAPI stains
FIG. 5 shows hair spheres from individual hair follicles. Well formed hair sphere can form after culture individual hair shafts in hESC medium for 2-4 weeks.
Panel A. Cell proliferation in telogen bulge after 10 days culture in hESC medium
Panel B. Well formed hair sphere formed in area 1-2 mm above the anagen bulb after 20 days
Panel C. Some hair sphere attached to the plate after 20 days
Panel D. Nestin stain shows some of cells within the hair sphere are positive
Panel E. Oct4 stain shows some of the cells within the hair sphere are positive

DESCRIPTION OF PREFERRED EMBODIMENTS

Human adult multipotent stem cells can be isolated from human hair follicles. These cells have the potential for differentiation to numerous cell types. Accordingly, these cells represent a new source of useful cells and methods of isolating them from hair follicles provides a convenient, readily available source of stem cells.

Human adult multipotent stem cells such as those derived from hair follicles by the method of the present invention can give rise to a number of different types of differentiated cells including neuronal cells, glial cells, melanocytic cells and smooth muscle cells. This ability is one factor that distinguishes them from previously reported stem cells which were derived from hair follicles described in U.S. Pat. No. 5,556,783. Human adult multipotent stem cells such as those derived from hair follicles by the method of the present invention can grow in spheres when cultured in medium that can support and maintain hESC as undifferentiated cells Human adult multipotent stem cells derived from bone marrow grow as flat sheets. Various markers have been detected on human adult multipotent stem cells such as those derived from hair follicles by the method of the present invention. In some embodiments, these markers include Nestin. In some embodiments, these markers include Oct4. In some embodiments, these markers include nanog. In some embodiments, these markers include Nestin and Oct4. In some embodiments, these markers include Nestin and nanog. In some embodiments, these markers include Oct4 and nanog. In some embodiments, these markers include Nestin, Oct4 and nanog. In addition, other markers which can also be expressed include Snail, Slug, Twist, and Sox9. The human embryonic stem cell markers stage specific embryonic antigen-3 and stage specific embryonic antigen-4 are generally not present.

Isolated populations of cells that include human adult multipotent stem cells such as those derived from hair follicles by the method of the present invention can be heterogenous. Cells may include one or more cells types from the following group: cells that express Nestin; cells that express Oct4; cells that express nanog; cells that express Nestin and Oct4; cells that express Nestin and nanog; cells that express Oct4 and nanog; and cells that express Nestin, Oct4 and nanog. In addition, the various cell may express other markers such as Snail, Slug, Twist, and Sox9. Some of the cells are free of the human embryonic stem cell markers stage specific embryonic antigen-3 and stage specific embryonic antigen-4.

Hair follicle derived stem cells according to the invention can be isolated from hair follicles or are the progeny cells of stem cells that were so isolated. Such cells therefore include those which were not themselves isolated from hair follicles but which trace their lineage to such cells.

The methods of the invention for preparing human multipotent stem cells include steps in which cells are obtained from the hair follicle and the multipotent stem cells of the invention are isolated. In some embodiments, the methods comprise forming a single cell suspension of cells from a sample that includes a hair follicle and culturing such cells in medium which can maintain and support culturing of hESCs as undifferentiated cells. Under such conditions, a hair sphere forms that comprise the population of cells of the present invention. In some embodiments, the methods comprise forming a single cell suspension of cells from a sample that includes a hair follicle and culturing such cells in a minimal serum free medium which cannot maintain and support culturing of hESCs but which comprises epidermal growth factor and bFGF. Under such conditions, a hair sphere forms that comprise the population of cells of the present invention. Alternatively, the hair follicle may be cultured in either the medium which can maintain and support culturing of hESCs as undifferentiated cells or the minimal serum free medium which cannot maintain and support culturing of hESCs but which comprises epidermal growth factor and bFGF. Cells which grow include a mass of cells that include the population of cells of the present invention.

In some preferred embodiments, human scalp tissues is trimmed and treated with dispase (for example 0.48 g/100 ml in DMEM) over night to free hair follicles from dermal tissue. The isolated hair follicles may washed such as with PBS to clear any contaminating dermal tissue and then treated with about 0.1% trypsin for about 20-30 minutes to disassociate the follicular epithelium from hair shaft. The material is filtered to form single cell suspension. The dissociated single cells can be cultured in hESC medium such as that consisting of about 80% Knockout DMEM/F-12 medium (Invitrogen, Carlsbad, Calif.), about 20% Knockout serum replacer (Invitrogen), about 200 mM L-glutamine (Invitrogen), about 0.1 mM β-mercaptoethanol (Sigma, St. Louis, Mo.), about 1% non-essential amino acids (Invitrogen), and about 4 ng/ml bFGF (Research Diagnostics, Flanders, N.J.). The medium is conditioned by using it for about 48 hr as growth medium for mouse embryonic fibroblasts. The conditioned medium is mixed with fresh hESC medium at a about 3:1 ratio, sterilized by filtration, and supplemented with additional bFGF at about 4 ng/ml before use. Single cells attach and form small adhesive aggregates, usually in about 3 days. These spheres, termed hair spheres, share similar morphology with embryoid bodies derived from hESCs under mouse feeder cell-free growth conditions. Hair spheres are well formed after 6 weeks. Approximately 1 in 100,000 seeded follicular cells is capable of forming a hair sphere.

In some preferred embodiments, human scalp tissues is trimmed and treated with dispase (for example 0.48 g/100 ml in DMEM) over night to free hair follicles from dermal tissue. The isolated hair follicles may washed such as with PBS to clear any contaminating dermal tissue and then treated with about 0.1% trypsin for about 20-30 minutes to disassociate the follicular epithelium from hair shaft. The material is filtered to form single cell suspension. The dissociated single cells can be cultured in medium containing DMEM-F-12 (3:1 conditioned to fresh), about 20 ng/ml EGF and about 40/ng ml bFGF. Single cells attach and form small adhesive aggregates, usually in about 3 days. These spheres, termed hair spheres, share similar morphology with embryoid bodies derived from hESCs under mouse feeder cell-free growth conditions. Hair spheres are well formed after 6 weeks. Approximately 1 in 100,000 seeded follicular cells is capable of forming a hair sphere.

In some preferred embodiments, human scalp tissues is trimmed and treated with dispase (for example 0.48 g/100 ml in DMEM) over night to free hair follicles from dermal tissue. The isolated hair follicles may washed such as with PBS to clear any contaminating dermal tissue and then treated with about 0.1% trypsin for about 20-30 minutes to disassociate the follicular epithelium from hair shaft. The material is filtered to form single cell suspension. The dissociated single cells can be cultured in hESC medium such as that consisting of about 80% Knockout DMEM/F-12 medium (Invitrogen, Carlsbad, Calif.), about 20% Knockout serum replacer (Invitrogen), about 1 mM L-glutamine (Invitrogen), about 0.1 mM β-mercaptoethanol (Sigma, St. Louis, Mo.), about 1% non-essential amino acids (Invitrogen), and about 0.5 g/mil mouse noggin (R&D Systems). Single cells attach and form small adhesive aggregates, usually in about 3 days. These spheres, termed hair spheres, share similar morphology with embryoid bodies derived from hESCs under mouse feeder cell-free growth conditions. Hair spheres are well formed after 6 weeks. Approximately 1 in 100,000 seeded follicular cells is capable of forming a hair sphere.

In some preferred embodiments, isolated hair follicles are cultured in hESC medium such as that consisting of about 80% Knockout DMEM/F-12 medium (Invitrogen, Carlsbad, Calif.), about 20% Knockout serum replacer (Invitrogen), about 200 mM L-glutamine (Invitrogen), about 0.1 mM β-mercaptoethanol (Sigma, St. Louis, Mo.), about 1% non-essential amino acids (Invitrogen), and about 4 ng/ml bFGF (Research Diagnostics, Flanders, N.J.). The medium is conditioned by using it for about 48 hr as growth medium for mouse embryonic fibroblasts. The conditioned medium is mixed with fresh hESC medium at a about 3:1 ratio, sterilized by filtration, and supplemented with additional bFGF at about 4 ng/ml before use. Cells continue grow on the hair follicle including aggregates of cells that include populations according to the invention. The cell aggregates may be used as a source from the cells of the invention are isolated.

In some preferred embodiments, isolated hair follicles are cultured in medium containing DMEM-F-12 (3:1 conditioned to fresh), about 20 ng/ml EGF and about 40/ng ml bFGF. Cells continue grow on the hair follicle including aggregates of cells that include populations according to the invention. The cell aggregates may be used as a source from the cells of the invention are isolated.

In some preferred embodiments, isolated hair follicles are cultured in hESC medium such as that consisting of about 80% Knockout DMEM/F-12 medium (Invitrogen, Carlsbad, Calif.), about 20% Knockout serum replacer (Invitrogen), about 200 mM L-glutamine (Invitrogen), about 0.1 mM β-mercaptoethanol (Sigma, St. Louis, Mo.), about 1% non-essential amino acids (Invitrogen), and about 0.5 g/ml mouse noggin (R&D Systems). Cells continue grow on the hair follicle including aggregates of cells that include populations according to the invention. The cell aggregates may be used as a source from the cells of the invention are isolated.

In some preferred embodiments, a sample of pancreatic, liver, heart or brain tissues is trimmed, washed such as with PBS, and then treated with about 0.1% trypsin for about 20-30 minutes to disassociate the cells. The material is filtered to form single cell suspension. The dissociated single cells can be cultured in hESC medium such as that consisting of about 80% Knockout DMEM/F-12 medium (Invitrogen, Carlsbad, Calif.), about 20% Knockout serum replacer (Invitrogen), about 200 mM L-glutamine (Invitrogen), about 0.1 mM β-mercaptoethanol (Sigma, St. Louis, Mo.), about 1% non-essential amino acids (Invitrogen), and about 4 ng/ml bFGF (Research Diagnostics, Flanders, N.J.). The medium is conditioned by using it for about 48 hr as growth medium for mouse embryonic fibroblasts. The conditioned medium is mixed with fresh hESC medium at a about 3:1 ratio, sterilized by filtration, and supplemented with additional bFGF at about 4 ng/ml before use.

In some preferred embodiments, a sample of pancreatic, liver, kidney, heart or brain tissues is trimmed, washed such as with PBS, and then treated with about 0.1% trypsin for about 20-30 minutes to disassociate the follicular epithelium from hair shaft. The material is filtered to form single cell suspension. The dissociated single cells can be cultured in medium containing DMEM-F-12 (3:1 conditioned to fresh), about 20 ng/ml EGF and about 40/ng ml bFGF.

In some preferred embodiments, a sample of pancreatic, liver, kidney, heart or brain tissues is trimmed, washed such as with PBS, and then treated with about 0.1% trypsin for about 20-30 minutes to disassociate the cells. The material is filtered to form single cell suspension. The dissociated single cells can be cultured in hESC medium such as that consisting of about 80% Knockout DMEM/F-12 medium (Invitrogen, Carlsbad, Calif.), about 20% Knockout serum replacer (Invitrogen), about 200 mM L-glutamine (Invitrogen), about 0.1 mM β-mercaptoethanol (Sigma, St. Louis, Mo.), about 1% non-essential amino acids (Invitrogen), and about 0.5 g/ml mouse noggin (R&D Systems).

Some aspects of the present invention relate to uses of such cells and populations of cells. Numerous uses of hESCs and other types of adult SCs have been described. The present invention relates to methods of using human multipotent adult stem cells. In some embodiments, the methods comprise administering the various cells described herein in methods of treating diseases disorders or injuries. In such embodiments, the human multipotent adult stem cells are induced to differentiate prior to administration into a human or they differentiate after administration. Cells may be administered free of any containment or coating directly into tissue, as part of a matrix or in a container. In some embodiments, the methods comprise using the various cells described herein in methods of treating diabetes. In such embodiments, the human multipotent adult stem cells are induced to differentiate into insulin producing cells prior to administration into a human or they differentiate into insulin producing cells after administration. Cells may be administered free of any containment or coating directly into tissue, as part of a matrix or in a container. In some embodiments, the methods comprise using the various cells described herein in methods of treating cardiac muscle damage. In such embodiments, the human multipotent adult stem cells are induced to differentiate into muscle cells. Generally they are introduced as stem cells directly into the heart, usually at or near the site of damage or scarring. Alternatively, they may be induced to differentiate prior to administration into a human. In some embodiments, the methods comprise using the various cells described herein in methods of treating muscle damage or disease. In such embodiments, the human multipotent adult stem cells are induced to differentiate into muscle cells. Generally they are introduced as stem cells directly into muscle tissue, usually at or near the site of damage or scarring. Alternatively, they may be induced to differentiate prior to administration into a human. In some embodiments, the methods comprise using the various cells described herein in methods of treating neurodegenerative diseases such as, for example, Parkinson's disease, Alzheimer's Disease, and Lou Gehrig's Disease (ALS). In such embodiments, the human multipotent adult stem cells are usually administered directly into the human such as into or in contact with the brain. Alternatively, they may be induced to undergo differentiation prior to administration into a human. Cells may be administered free of any containment or coating directly into tissue, as part of a matrix or in a container. In some embodiments, the methods comprise using the various cells described herein in methods of treating nerve damage such as, for example, spinal injury. In such embodiments, the human multipotent adult stem cells are usually administered directly into the human at or near the site of damage. Alternatively, they may be induced to undergo differentiation prior to administration into a human. Cells may be administered free of any containment or coating directly into tissue, as part of a matrix or in a container. In some embodiments, the methods comprise using the various cells described herein in methods of treating bone loss, damage and/or disease. In such embodiments, the human multipotent adult stem cells are usually administered directly into the human at or near the site of damage. Alternatively, they may be induced to undergo differentiation prior to administration into a human. In some embodiments, the methods comprise using the various cells described herein in methods of treating cartilage loss, damage and/or disease. In such embodiments, the human multipotent adult stem cells are usually administered directly into the human at or near the site of damage. Alternatively, they may be induced to undergo differentiation prior to administration into a human. In some embodiments, the methods comprise using the various cells described herein in methods of treating hair loss. In such embodiments, the human multipotent adult stem cells are usually administered directly into the human scalp. Alternatively, they may be induced to undergo differentiation prior to administration into a human. In some embodiments, the methods comprise using the various cells described herein in methods of treating immune disorders. In such embodiments, the human multipotent adult stem cells are usually administered directly into the human. Alternatively, they may be induced to undergo differentiation prior to administration into a human. In some embodiments, the methods comprise using the various cells described herein in methods of treating diseases associated with a non-functioning, underfunctioning, or defective gene. In some embodiments, the methods comprise using the various cells described herein in methods of treating diseases with a treatment that provides a therapeutic protein to the individual. In such embodiments, genetic material is inserted into the human multipotent adult stem cells prior to their administration into the individual. Cells may be administered free of any containment or coating directly into tissue, as part of a matrix or in a container. In some embodiments of the present invention, no genetic material is inserted into the human multipotent adult stem cells prior to their use or administration into the individual.

The present invention provides media for culturing adult multipotent stem cells such as hair follicle derived human adult multipotent stem cells, pancreatic derived human adult multipotent stem cells, liver derived human adult multipotent stem cells, kidney derived human adult multipotent stem cells, heart derived human adult multipotent stem cells and brain derived human adult multipotent stem cells. In one embodiment, the medium comprises minimal serum free media such as Knock-Out™ DMEM/F-12 medium (Invitrogen, Carlsbad, Calif.) supplemented with basic Fibroblast growth factor (preferably about 4 ng/ml) and epidermal growth factor (preferably about 20 ng/ml). In one embodiment, the medium comprises minimal serum free media such as about 80% Knock-Out™ DMEM/F-12 medium (Invitrogen, Carlsbad, Calif.) supplemented with about 20% Knockout serum replacer (Invitrogen), L-glutamine (Invitrogen) (preferably about 200 mM), 0.1 mM β-mercaptoethanol (Sigma, St. Louis, Mo.) (preferably about 0.1 mM), non-essential amino acids (Invitrogen) (preferably about 1%) and bFGF (Research Diagnostics, Flanders, N.J.) (preferably about 4 ng/ml). In one embodiment, the medium comprises minimal serum free media such as about 80% Knock-Out™ DMEM/F-12 medium (Invitrogen, Carlsbad, Calif.) supplemented with about 20% Knockout serum replacer (Invitrogen), L-glutamine (Invitrogen) (preferably about 200 mM), 0.1 mM β-mercaptoethanol (Sigma, St. Louis, Mo.) (preferably about 0.1 mM), non-essential amino acids (Invitrogen) (preferably about 1%) and mouse noggin (R & D Systems) (preferably about 0.5 g/ml)

EXAMPLES

Example 1

In experiments that were performed in an attempt to isolate melanocyte precursor cells, isolated cells were discovered to have multiple differentiation potential in addition to melanocytes. The cells that were isolated are capable of self renewal and they express transcription factors seen in pluripotent embryonic stem cells and embryonic neural crest stem cells. These cells are located in the bulge area of hair follicles. These cells have been isolated and constitute an isolated multipotent adult stem cell population derived from human hair follicles.

Figure 1:
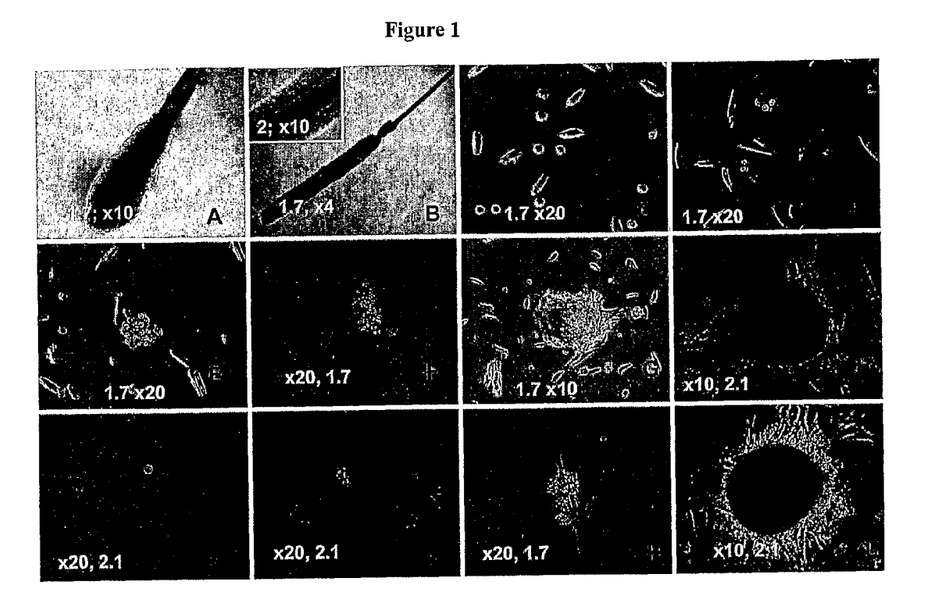
FIG. 1 shows data form hair spheres and limiting dilution assay. Scalp tissues were treated with dispase overnight and hair follicles were plucked and washed extensively to rid of any dermal contamination. Then the hair follicles were treated with typsin. In limiting dilution assay, single cells from a hair sphere is diluted to ensure some of the wells in 96 well plate have only one cell.

Excess human scalp tissues were procured through CHTN. The tissues were trimmed and treated with dispase (0.48 g/100 ml in DMEM) over night to free hair follicles from dermal tissue. The isolated hair follicles were washed extensively with PBS to clear any contaminating dermal tissue (FIG. 1) and then treated with 0.1% trypsin for 20-30 minutes to disassociate the follicular epithelium from hair shaft and filtered to form single cell suspension. Dissociated single cells from 9 patients were cultured in hESC medium consisting of 80% Knockout DMEM/F-12 medium (Invitrogen, Carlsbad, Calif.), 20% Knockout serum replacer (Invitrogen), 200 mM L-glutamine (Invitrogen), 0.1 mM β-mercaptoethanol (Sigma, St. Louis, Mo.), 1% non-essential amino acids (Invitrogen), and 4 ng/ml bFGF (Research Diagnostics, Flanders, N.J.). This medium was conditioned by using it for 48 hr as growth medium for mouse embryonic fibroblasts.

hESC medium conditioned by mouse embryonic fibroblasts was mixed with fresh hESC medium at a 3:1 ratio, sterilized by filtration, and supplemented with additional bFGF at 4 ng/ml before use. Alternatively, single cells were cultured in medium containing DMEM-F-12 (3:1), 20 ng/ml EGF and 40/ng ml bFGF. Single cells attached and formed small adhesive aggregates in 3 days. These spheres, which we termed hair spheres, shared similar morphology with embryoid bodies derived from hESCs under mouse feeder cell-free growth conditions. Hair spheres were well formed after 6 weeks. Approximately 1 in 100,000 seeded follicular cells is capable of forming a hair sphere.

Limiting dilution assays were performed in 96 well plate. After separating a clonally-derived hair sphere into single cells and reseeding at a concentration of 1 cell/well, some of the wells have single cells attached, which remained as a single cell 8 hr after seeding in hESC medium. Proliferation starts 24 hrs after seeding and small aggregates developed from a single cell after 7 days and a well formed sphere after 8 weeks. This process can be repeated without losing sphere formation capability, which demonstrates that these cells are capable of self renew.

Figure 2:
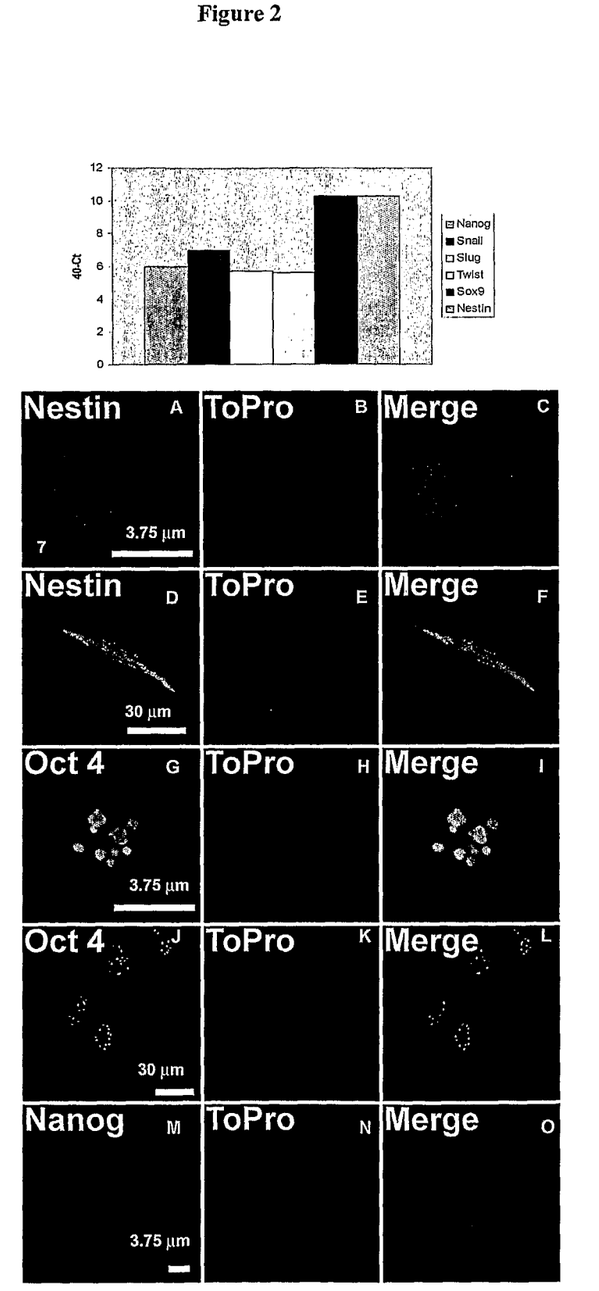
FIG. 2 shows that Hair sphere derived cells express stem cell markers. Hair spheres were disassociated, plated and stained with various antibodies. Gene expression of hair spheres was evaluated by real time PCR.

It has long been postulated that hair harbors neural crest stem cells that give rise to melanocytes. In addition, recent studies showed that mouse and human dermis derived stem cells are distinct from mesenchymal stem cells, and CNS neural stem cells, but similar to embryonic neural crest stem cells (NCSCs). Therefore, hair spheres were analyzed for expression of genes associated with embryonic NCSCs. Real time RT-PCR analysis showed that hair spheres expressed the transcription factor genes slug, snail, Twist and Sox9; and also neural stem cell marker Nestin (FIG. 2). Some of the spheres also expressed Nanog mRNA, a transcription factor that has only been shown expressed in pluripotent embryonic stem cells. Hair sphere derived cells were stained to detect Oct4 and Nanog, transcription factors involved in embryonic stem cell self renew. About 5% cells, a majority of them were small round cells with a few larger cells were positive for Oct4 which showed punctate nuclear staining pattern. Nanog stained only a fraction of Oct4 positive cells and all of these were in small round cells. Some of the small round cells can be double labeled with Oct4 and Nanog. Nestin stains about 15% of cells which included cells with a variety of morphology. These results suggest that the small round cells are very immature cells. The isolated cells constituted a population of adult stem cells that express both Oct4 and Nanog. However, unlike embryonic stem cells, these small round cells did not express stage specific embryonic antigen (SSEA)-3 and -4, indicating that these are a unique population of stem cells.

Figure 3A:
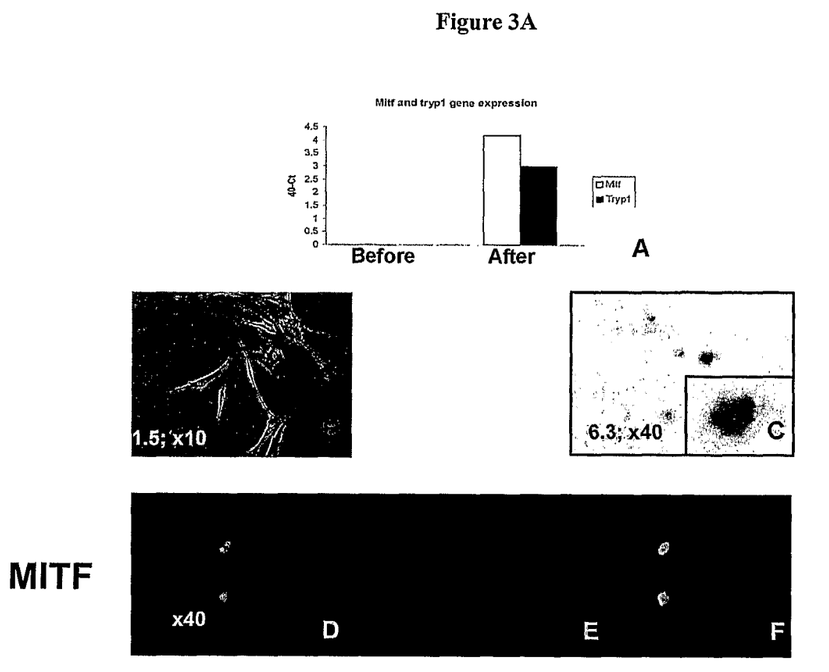
FIG. 3A shows Melanocytic differentiation of hair sphere derived cells. Hair sphere derived cells were incubated in the melanocyte differentiation medium. Functional study was performed using skin reconstruct.
Figure 3B:
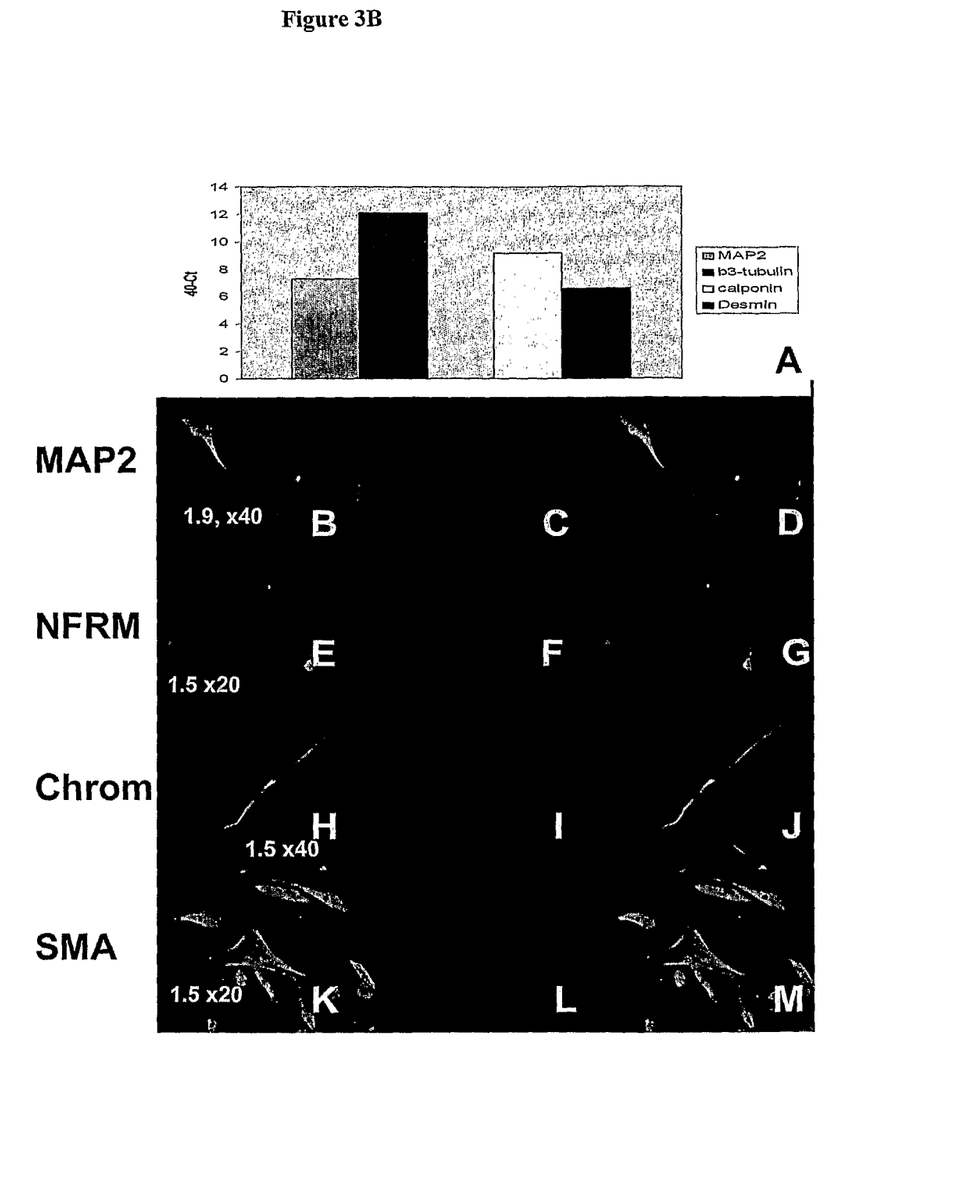
FIG. 3B shows Neuron and smooth muscle differentiation. Hair sphere derived cells were incubated in the neuron or smooth muscle differentiation medium.
Figure 4:
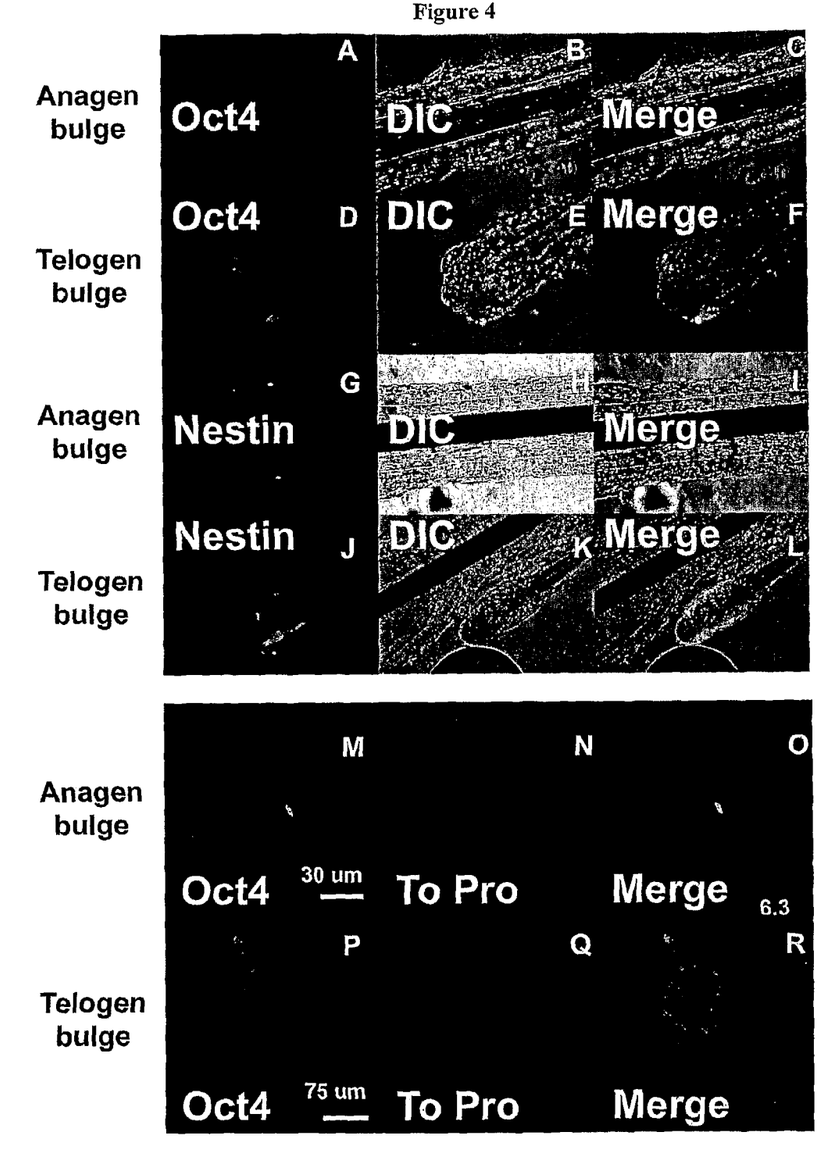
Figure 5:
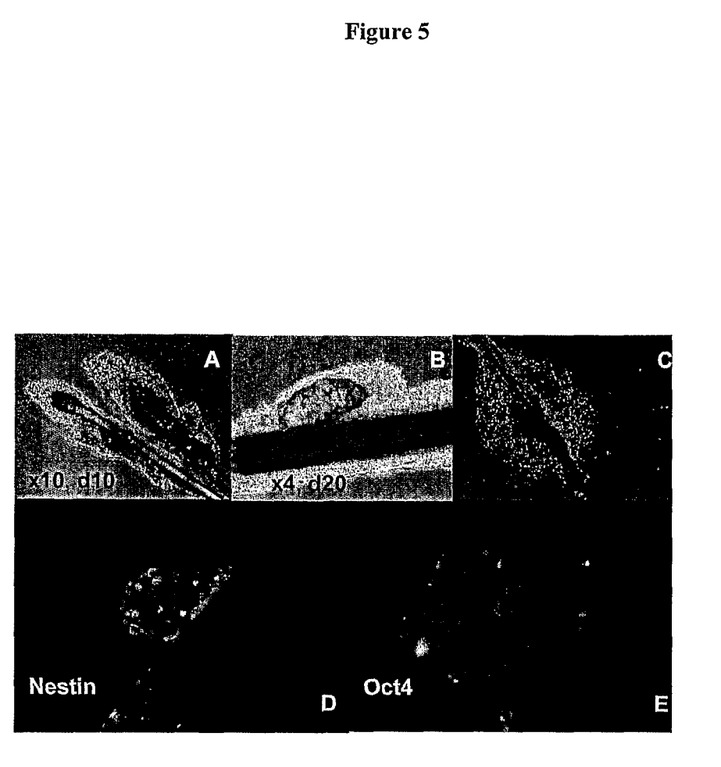

The in vitro differentiation capacity of hair spheres was assessed. Undifferentiated hair spheres cultured in hESC medium did not express any lineage specific genes such as Mitf, tryp1, Map2, β3-tubulin, calponin or desmin by real time PCR or keratin by immunostaining. Dissociated hair sphere cells were plated in fibronectin coated plate in melanogenic differentiation medium (contains dexamethasone (0.05 μM; Sigma, St. Louis, Mo.), insulin-transferrin-selenium (1×; Sigma), linoleic acid-bovine serum albumin (1 mg/ml; Sigma), low-glucose DMEM (30%; Life Technologies, Rockville, Mass.), MCDB 201 (20%; Sigma), L-ascorbic acid ($10^{-4}$ M; Sigma), conditioned media of mouse L-Wnt3a cells (ATCC, Manassas, Va.) (Wnt3a-CM; 50%), Stem cell factor (SCF) (50-100 ng/ml; R&D System, Minneapolis, Minn.), Endothelin-3 (100 nM; American Peptide, Sunnyvale, Calif.), cholera toxin (20 μM; Sigma), the phorbol ester 12-O-tetradecanoylphorbol-13-acetate (50 nM; Sigma), and basic fibroblast growth factor (bFGF; 4 ng/ml; Life Technologies, Fang et al unpublished data). Attached cells developed dendritic processes and melanin pigment appeared several days after differentiation. Differentiated cells were positive for Mitf and Tryp1 by real time PCR and Mitf by immunocytochemistry. These cells produced abundant melanin pigment as demonstrated by Fontana-Mason stain (FIG. 3).

To further study the function of hair sphere derived melanocytes, these cells were introduced into skin reconstructs. These cells homed to the epidermal dermal junction, expressed tyrosinase and produced melanin pigment similar to normal melanocytes, indicating that hair sphere derived melanocytes not only express melanocytic markers but also interact with squamous cells and dermal collagen similar normal melanocytes.

To determine whether hair spheres could generate cells not seen in skin, hair sphere derived cells were cultured in slides coated with Matrigel or poly-D-lysine/laminin, and incubated in neuronal differentiation medium (DMEM-F12 (3:1) supplemented with 40/ng ml FGF2 and 10% FBS (Biowhittaker, Walkersville, Md.) for 5-7 days. Cells were then cultured for an additional 5-7 days in the same medium without FGF2, but with the addition of 10 ng/ml nerve growth factor, 10/ng ml brain-derived neurotrophic factor (BDNF; Peprotech, Rocky Hill, N.J.) and 10 ng/ml NT3 (Peprotech)). After 2-3 weeks of incubation, about 10% of cells showed long dendritic processes and expressed MAP2 and β3 tubulin by real time PCR and neurofilament (NFRM), MAP2 and chromogranin by immunocytochemical stains. MAP2 stained mostly the dendritic process but not the cell body, characteristic of neurons.

To assess whether hair spheres can differentiate into cells other than neuroectoderm, hair sphere derived cells were cultured in poly-D-lysine/laminin coated chamber slides in smooth muscle differentiation medium. Under these conditions for 2 weeks, differentiated cells expressed calponin and desmin by PCR and strongly positive for smooth muscle actin (SMA), indicating smooth muscle differentiation. The contraction ability of these hair sphere derived smooth muscle cells was analyzed by mixing these cells with collagen. These cells could contract collagen similar to normal vascular smooth muscle cells, indicating that these cells have acquired function similar to smooth muscle cells. These results indicate that hair sphere derived cells are capable to differentiate into neuroectoderm and mesoderm lineages.

To investigate the localization of these multipotent stem cells in the hair, human scalp tissue was stained to detect Nestin and Oct4 by immunuhistochemistry. No specific staining in the hair follicles was identified. Scalp tissues were treated with dispase overnight and individual hair follicles were plucked and cultured in hESC cells medium. Unlike stem cells emigrant from mouse whisker hair bulge explants, emigration of cells were not observed within first week. Instead, telogen bulges slightly increased in size after 6 days. Individual hairs were stained to detect Nestin and Oct4 and showed that there were Oct4 and Nestin positive cells in telogen bulges. In addition, rare positive cells were also located 1-2 millimeter from the bulb, which appeared to coincide with the anagen bulge. The results indicate that the multipotent stem cells are located in the stem cell niches in the hair follicles.

These data demonstrated a previously unknown population of multipotent stem cells within human hair follicles that are significantly different than epithelial stem cells. These cells can be isolated, cultured and expanded as hair spheres, during which time they maintain their multipotentiality in the hESC medium. These stem cells persist into late adulthood and have neuroectoderm and mesoderm differentiation potential in vitro. These cells are located in the bulge area of hair follicles, a well defined stem cell niche. Further, hESC medium can be used to isolated adult stem cells.

The implications of our findings are broad. First, we demonstrated that human hair follicle contains a previously unknown multipotent stem cells that can differentiated into melanocytes and cell types never found in their tissue of origin, in this case neurons and smooth muscle cells. Our findings suggest that melanocytes and hair follicle associated pilar rector muscle might be derived from these cells. Second, this adult stem cell population uniquely expresses Oct4 and Nanog, and Nanog is positive in a subpopulation of Oct4 which is similar to what has been reported in embryonic stem cells, indicating that these cells express similar transcription factors as embryonic stem cells. Third, cells in the hair sphere also express Snail, Slug, Twist, Sox9 and Nestin indicate that hair sphere is composed of a heterogeneous population of cells and they are at different differentiation stages. Fourth, hair bulge is a well defined stem cell niche for epithelial stem cells; we now showed that bulge is probably also the niche for these newly discovered multipotent stem cells. The unique property of hair bulge to maintain stem cell population over life span of mammals by providing an environment presumably maintain stem cell potential in vivo is intriguing and deserve more studies. Fifth, human scalp tissue is relatively easy to procure, and hair follicles are a new source for adult stem cells, which can be potentially used for individualized cell based therapeutic strategies.

Example 2

Method of Treating Diabetes and Replacing Islet Cells with SCs

U.S. Pat. No. 6,866,843, which is incorporated herein by reference, describes methods of transplanting in a mammal and treating diabetes mellitus by administering a pseudo-islet like aggregate differentiated from a nestin-positive pancreatic stem cell. The isolated cells and populations of cells of the present invention may be used in such methods. For example, the adult multipotent stem cells are first isolated from hair follicles and used in the method set forth in U.S. Pat. No. 6,866,843.

Example 3

Method of Regenerating Myocardium

U.S. Pat. No. 6,015,671, which is incorporated herein by reference, and Yoon, et al., J Clin Invest. 2005 "Clonally expanded novel multipotent stem cells from human bone marrow regenerate myocardium after myocardial infarction" which are each incorporated herein by reference describe the use of stem cells to treat patients who have damaged heart muscles. Stem cells are implanted directly into the heart where they develop into cardiac muscle tissue. The isolated cells and populations of cells of the present invention may be used in such methods. For example, the adult multipotent stem cells are first isolated from hair follicles and used in the method set forth in U.S. Pat. No. 6,015,671.

Example 4

Method of Replacing Deficient Neuronal or Glial Cell Populations

U.S. Application Serial Number 20020164308, which is incorporated herein by reference, describes the use of stem cells. For example, methods of inducing somatic differentiation of stem cells into progenitor cells are described. In such methods, undifferentiated embryonic stem cells are first obtained and then provided with a differentiating signal under conditions which are non-permissive for stem cell renewal, do not kill cells and/or induces unidirectional differentiation toward extraembryonic lineages. The isolated cells and populations of cells of the present invention may be used in such methods in place of the embryonic stem cells. Thus the method would include first obtaining such cells. Methods of transplanting ES derived neural progenitor cells in a host are also described. Such methods comprise obtaining a source of neural progenitor cells, culturing the neural progenitor cells in the presence of serum free medium supplemented with growth factors including, and injecting the neural progenitor cells into the nervous system of the host. In some embodiments, the neural progenitor cells are injected into the lateral cerebral ventricle of the nervous system. In addition, methods of producing stable grafts of neural cells and contributing in the histogenesis of a living host are described. as are methods of modifying the nervous system of a host, including any one of replacing deficient neuronal or glial cell populations, restoring deficient functions or activating regenerative and healing processes in the nervous system to regenerate cell populations. The isolated cells and populations of cells of the present invention may be used in such methods. For example, the adult multipotent stem cells are first isolated from hair follicles and used in the method set forth in U.S. Application Serial Number 20020164308.

Example 5

Method of Treating a Congenital Disease

U.S. Application Serial Number 20020160509, which is incorporated herein by reference, describes methods of preventing and treating a congenital diseases. The adult multipotent stem cells are first isolated from hair follicles and used in the method set forth in U.S. Application Serial Number 20020160509.

Example 6

Method of Transplanting SCs

There are numerous uses for multipotent stem cells, many of which have been envisioned with hESCs in mind but which can be achieved using the cells of the present invention. U.S. Application Serial Number 20020068045, which is incorporated herein by reference, describes methods of transplanting ES derived neural progenitor spheres comprising: disaggregating the spheres and injecting the disaggregated spheres into a living host. The cells and spheres of the present invention can be used in such methods in place of the embryonic spheres. Also described as methods of producing a stable graft of neural cells and contributing in the histogenesis of a living host said method comprising: including for use to treat pathological conditions such as neurodegenerative disorders, vascular conditions, autoimmune disorders, congenital disorders, and trauma. The cells and spheres of the present invention provide an alternative source of cells which can be used.

Example 7

Subpopulation of the pluripotent stem cells present in the inner cell mass of the pre-implantation embryo might never differentiate, but instead may persist and seed adult tissues.

Such rare pluripotent cells may be responsible for recent observations of unexpected adult somatic tissue plasticity.

To identify and isolate Adult pluripotent stem cells from adult tissue samples, medium specifically designed to growth embryonic stem cells may be used to expand adult stem cells. Examples of such medium include: 1). Human ESC medium consisted of 80% Knockout DMEM/F-12 medium (Invitrogen), 20% Knockout serum replacer (Invitrogen), 200 mM L-glutamine (Invitrogen), 0.1 mM β-mercaptoethanol (Sigma), 1% non-essential amino acids (Invitrogen), and 4 ng/ml bFGF (Research Diagnostics). This medium is conditioned by using it for 48 hr as growth medium for mouse embryonic fibroblasts (MEFs). Human ESC medium conditioned by MEFs is mixed with fresh hESC medium at a 3:1 ratio, sterilized by filtration, and supplemented with additional bFGF at 4 ng/ml before use; or 2) 80% DMEM/F12 and 20% KNOCKOUT serum replacement, and was supplemented with 1 mM L-glutamine, 1% nonessential amino acids (all from Invitrogen) and 0.1 mM 2-mercaptoethanol (Sigma) with 0.5 g/ml mouse noggin (R&D Systems) or 40 ng/ml human bFGF (Invitrogen).

Pancreas, liver, brain, kidney and heart tissue is enzymatically disassociated and cultured in the above medium. Cell aggregates (spheres) will form after several days of incubation. These sphere forming cells are putative stem cells from each organ. The spheres can be expanded in vitro to produce enough cells for transplantation. In addition, genetic modifications can be made by transfect specific genes into to the stem cell population, such as Erythropoitin gene into kidney stem cells; insulin gene into pancreas stem cells, normal Huntington gene (Huntington disease protein) into patients with Huntington's disease etc. As stem cell proliferate, these genes will be transmitted to the differentiated cells, and differentiated cells can acquire normal functions.

Isolated adult stem cells can be expanded in vitro and, in some embodiments, either injected back the site of origin, or subcutaneously such as pancreatic beta cells, EPO producing kidney cells etc. for easy monitoring of cell growth.

Example 8

Mesenchymal Differentiation: Adipocyte, Osteocyte and Chondrocyte

Attached hair sphere cells were cultured in respective mediums for 7-14 days and examined for specific differentiation marker expression. Hair sphere-derived stem cells differentiated into adipocytes, osteocytes and chondrocytes.

Adipogenesis was induced in differentiation medium containing 90% low-glucose DMEM (Invitrogen), 1×ITS (Sigma), 1 mg/ml LA-BSA (Sigma), 1 μM hydrocortisone (Sigma), 60 μM indomethacin (Sigma), 0.5 mM isobutylmethylxanthine (Sigma), 10% horse serum (Invitrogen), and evaluated by Oil Red O adipogenic staining. Oil red staining showed oil droplets in the cytoplasma of the differentiated cells.

Osteogenesis was induced in differentiation medium containing 90% low-glucose DMEM (Invitrogen), 1×ITS (Sigma), 1 mg/ml LA-BSA, (Sigma) 0.1 μM dexamethasone (Sigma), 0.05 M L-ascorbic acid-2-phosphate (AsAP) (Sigma), 10 mM b-glycerophosphate, (Sigma) 10% FCS (BenchMark), and evaluated by alkaline phosphatase histochemistry staining. Alkaline phosphatase staining showed a number of positive cells.

Chondrogenesis was induced in medium containing 90% DMEM (Invitrogen), 1×ITS (Sigma), 1 mg/ml LA-BSA (Sigma), 0.05 μM dexamethasone (Sigma), 10 ng/ml TFG-b1 (R&D System), 1 mM pyruvate (Sigma), and evaluated by type II collagen chondrogenic immunostaining. Type II collagen staining was visualized with fluorescein labeled secondary antibody, and nucleus was stained with DAPI. The differentiated cells were positive for type II collagen, a marker for chondrocytes.

Example 9

Transplantation into Mouse Brain and Muscle In Vivo

Differentiated hair sphere cells express molecules compatible with neural and muscle phenotype. Differentiated hair sphere cells were transplanted into adult nude mouse brain and muscle without any further treatment.

Hair sphere-derived stem cells were expanded in hESC medium and then cultured in the neuron or muscle differentiation medium for 11 or 4 days, respectively. These cells were labeled by CFDA SE (Vybrant CFDA SE Cell Tracer Kit; Molecular Probes) as recommended by the manufacture. Briefly, attached hair cells were incubated in 10 uM of dye at 37° C. for 15 min, and exchanged to fresh culture medium for 30 min in 37° C. Labeled cells were harvested and counted.

Neural differentiated cells were injected unilaterally and stereotactically targeted to the subventricular zone in 4 nude mice through a Hamilton microsyringe ($1 \times 10^5$ cells in 3 ul of PBS). The injected mice were grown for another 28 days and then sacrificed. No behavior changes were seen in these mice. Brains were removed, equilibrated in 30% sucrose, embedded in cryo-embedding compound, frozen, cut into 10 μm thick cross sections, prepared for immunohistochemistry for neurofilament (NF) by using standard methods, and counterstained with 25 ng/ml 4-diamidino-2-phenylindole (DAPI). Implanted human cells were observed and images were captured by conventional fluorescence (single fluorescein or triple tube with fluorescein, Texas red and DAPI optics). The rat anti-NF antibody was visualized using a chick anti-rat secondary antibody labeled with Alexa Fluor 594 dyes (red). Dye-labeled human cells (green) were indeed present in all four injected mice, however, only a very small percentage of cells survived. Multiple brain sections from injecting site were examined (10-20 sections per mouse), and the range of survived human cells were 2 to 50 per mouse. Some of the human cells showed axon like structure. 70% of the dye-labeled human cells were positive for NF staining (FIG. 9), suggesting that the injected human cells can acquire neural phenotype in vivo. Frozen sections of mouse brain were viewed at 200×DIC. The same area was viewed under a fluorescent microscope, green cells are human hair cells labeled with CFDA SE. One cell in the center showed an axon like structure (200×, fluorescein tube, and 400×). The same area was viewed after NF staining, a few human cells were positive for both CFDA SE and NF stains, suggesting that the human hair cells acquire at least some neuron phenotypes (200×, fluorescein, texas red and DAPI triple tube, and enlarged to 400×). Morphology of an adjacent section were also viewed (200×, H&E).

Similarly, muscle differentiated cells (4 days differentiation) were labeled and injected into tibialis anterior ($1.5 \times 10^6$ cells in 20 ul of PBS) in 2 mice. Injected animals were grown for 28 days and then sacrificed. Tibialis anterior was dissected, embedded in cryo-embedding compound, frozen, cut into 5 μm thick cross sections and observed for dye-labeled human cells. Rare dye labeled cells were present (<5 per mice) and some acquired the morphology of skeleton muscle, suggesting again that injected human cells can acquire muscle phenotype in mouse in vivo. Frozen section of mouse tibialis anterior were viewed (200×, DIC) and the same area was viewed under a fluorescent microscope. Green cells were human cells labeled with CFDA SE, suggesting human hair stem cells can survive in mouse muscle (200×, fluorescein tube).

Example 10

Islet and Lymphocyte Differentiation

Adult stem cells are cultured to induce Islet and lymphocyte differentiation. Islet differentiation will produce cells that respond to and produce insulin. Such cells are useful to treat diabetes. Lymphocyte differentiation will produce immune cells useful in the treatment of immune disorders.

Adult stem cells are mixed with islet cells to induce islet differentiation. The cells are cultured to produce a population of islet cells that can be transplanted into the diabetic individual such as part of a device or cell matrix and/or directly into the tissue of an individual. Alternatively, adult stem cells are transplanted into the pancreas to induce islet differentiation.

The invention claimed is:

1. A method of preparing an isolated population of human hair-follicle derived multipotent adult stem cells comprising the steps of:
   a) incubating a human scalp sample with dispase to free hair follicles from dermal tissue;
   b) washing the free hair follicles of a);
   c) treating the follicles of b) with trypsin such that follicular epithelium is dissociated from hair shaft
   d) obtaining a single cell suspension from the dissociated follicular epithelium treated in step c;
   e) culturing said single cells in conditioned human embryonic stem cell (hESC) media wherein said hESC media is selected from the group consisting of
   i) DMEM/F-12 at 3 parts conditioned DMEM/F-12 medium to 1 part fresh medium, 20 ng/ml EGF and 40 ng/ml bFGF or
   ii) hESC medium consisting of about 80% Knockout DMEM/F-12 medium, about 20% Knockout serum replacer, about 200 mM L-glutamine, about 0.1 mM β-mercaptoethanol, about 1% non-essential amino acids, and about 4 ng/ml bFGF,
   said hESC media being conditioned via use as growth medium for mouse embryonic fibroblasts and being mixed with fresh hESC medium at about 3 parts conditioned hESC to 1 part fresh hESC, and supplemented with additional bFGF at about 4 ng/ml, such that hairspheres consisting of adhesive aggregates form from said single cells, wherein cells isolated from said hair spheres so cultured are multipotent stem cells which express Oct4 and Nanog but lack expression of SSEA-3 and SSEA-4 and
   (f) isolating said multipotent adult stem cells.

2. A method of preparing an isolated population of human hair-follicle derived multipotent adult stem cells comprising the steps of:
   a) incubating a human scalp sample with dispase to free hair follicles from dermal tissue;
   b) washing the free hair follicles of a);
   c) treating said hair follicles with trypsin, thereby dissociating follicular epithelium from hair shaft;
   d) obtaining a single cell suspension from the dissociated epithelium of step b);
   e) culturing said single cells in minimal serum free media supplemented with human basic fibroblast growth factor and human epidermal growth factor, such that hairspheres consisting of adhesive aggregates form from said single cells, wherein cells isolated from said hairspheres are multipotent stem cells which express Oct4 and Nanog but lack expression of SSEA-3 and SSEA-4.

* * * * *